United States Patent [19]

Kaczmarek et al.

[11] 4,155,247
[45] May 22, 1979

[54] MULTI-PART GAS SAMPLER

[75] Inventors: Thomas D. Kaczmarek, Penn Hills; Richard J. Wengrzyn, Edgewood, both of Pa.

[73] Assignee: Westinghouse Electric Corp., Pittsburgh, Pa.

[21] Appl. No.: 792,836

[22] Filed: May 2, 1977

[51] Int. Cl.² .................. G01N 15/06; B01D 50/00; B01D 53/30
[52] U.S. Cl. .................. 73/28; 73/421.5 R; 55/270; 55/316; 55/485; 55/502; 55/503
[58] Field of Search .......... 55/270, 316, 485, 486, 55/501–503, 482; 73/28, 421.5 R; 340/237 R; 310/68 B, 68 C

[56] References Cited

U.S. PATENT DOCUMENTS

| | | |
|---|---|---|
| 1,888,150 | 11/1932 | Walker .................. 55/503 |
| 2,251,964 | 8/1941 | Stackhouse .................. 55/486 |
| 3,109,724 | 11/1963 | Heckman et al. .................. 73/28 |
| 3,422,679 | 1/1969 | McGowan et al. .................. 55/270 |
| 3,528,279 | 9/1970 | Lasseur et al. .................. 55/270 |
| 3,972,225 | 8/1976 | Fort et al. .................. 73/28 |

Primary Examiner—Frank W. Lutter
Assistant Examiner—David L. Lacey
Attorney, Agent, or Firm—G. H. Telfer

[57] ABSTRACT

A dynamoelectric machine with a monitoring system for monitoring a gas stream causes a sample of the gas stream to be collected if its characteristics indicate that a material in the dynamoelectric machine is being thermally degraded. The sampling device will collect a sample of large particles, small particulates, and vapors and gases. The sampling device offers a low resistance to the flow of the gas stream for improved particulate and vapor collection.

3 Claims, 7 Drawing Figures

MULTI-PART GAS SAMPLER

BACKGROUND OF THE INVENTION

1. Field of the Invention

This invention relates to gas stream monitoring apparatus and particularly to such apparatus for use with gas-cooled dynamoelectric machines.

2. Description of the Prior Art

Large dynamoelectric machines occasionally fail due to thermal degradation of various materials, particularly organic insulation. Since an early detection of the insulation failure is essential to the prevention of a large scale burnout of the machine, monitoring devices are desirably used which monitor the gas streams that flow through dynamoelectric machines. Presently, most monitors work by detecting particulates in the gas stream, which are formed when insulation is being thermally degraded. When a monitor detects degradation products and generates a signal, the flow of the detectable particulates to the monitor is terminated to determine whether the signal is genuine or is due to a malfunction in the monitor. If the signal then terminates, it is assumed to be genuine and the dynamoelectric machine can be shut down for repair.

In U.S. Pat. No. 3,972,225 issued Aug. 3, 1976 it was disclosed that if the gas stream is sampled when the monitor indicates that a failure is occurring, the products collected can be analyzed to determine which material in the machine was failing. Since the location of the various materials is known, the search for the failure is considerably shortened.

It was also disclosed that the sampling can be done automatically, so that when the monitor produces a signal it can be checked for authenticity and a sample taken without human interference. In addition, it was disclosed that a particular sampling device, which separates the products of the gas streams into particles 10 microns or greater, particulates less than 10 microns, and gases is particularly useful in facilitating the analysis.

Data has been collected which shows that the pressure drop across the dynamoelectric machine's monitor used in the field is very low. The pressure drop across the vapor collector component of the disclosed vapor trap is about 9 psi at a hydrogen flow rate of 3.5 liters per minute. Because such a high head pressure is required to maintain gas flow through the vapor trap, there is an adverse effect on the particulate trap in that the particulate density is lower under the high head pressure.

In U.S. Pat. No. 3,972,225 the vapor collection trap is a column of adsorbing material such as activated charcoal, silica gel, alumina, etc., (but a modified ethylvinyl benzene-divinylbenzene copolymer sold by Waters Company under the trade name "PORAPAK R" is used). This column of adsorbing material is approximately $\frac{1}{4}$" in diameter by about $1\frac{1}{2}$" long.

SUMMARY OF THE INVENTION

We have found that taking an identical volume of the adsorbing material used in U.S. Pat. No. 3,972,225 and sandwiching it between two one inch diameter perforated stainless steel discs and placing the resulting thin layer, approximately 1" in diameter by 0.1 inch, in thickness in a one inch line filter that the gas flow resistance of this assembly drops to essentially zero.

Taking the improved vapor sampler and installing it on a dynamoelectric machine having a gas stream, a gas stream monitor and a sampling system which has a three part filter, one being a large particle filter for filtering particles greater than about 10 microns, a small particulate filter for filtering particulates less than 10 microns, and the disclosed vapor trap that has a low resistance to the flow of the gas stream and will adsorb vapors and gases, that there is an improved effectivity of the collection of not only the organic vapors but also the particulates.

This invention discloses a sampling system for sampling of organic particulates and vapors in a dynamoelectric machine's cooling gas system (or other gas system) that has an extremely low resistance to the flow of the cooling gas. Because of the extremely low resistance to the flow of the cooling gas, this invention is more effective in the collection of particulates and organic vapor than has been disclosed in the prior art. Since the vapor trap of this invention has nearly zero pressure drop across it (rather than the greater than 9 psi of the current art vapor trap) the sample gas from the generator drops in pressure before the trap, cooling the sample vapors and inducing particulation. In the present art, the greater than 9 psi "resistance" of the vapor trap maintains high sample stream pressures until after the gas stream has passed through the total trap assembly.

BRIEF DESCRIPTION OF THE DRAWINGS

For a better understanding of the invention, reference may be had to the preferred embodiments, exemplary of the invention, shown in the accompanying drawings in which.

DESCRIPTION OF THE PREFERRED EMBODIMENTS

Figure 1:
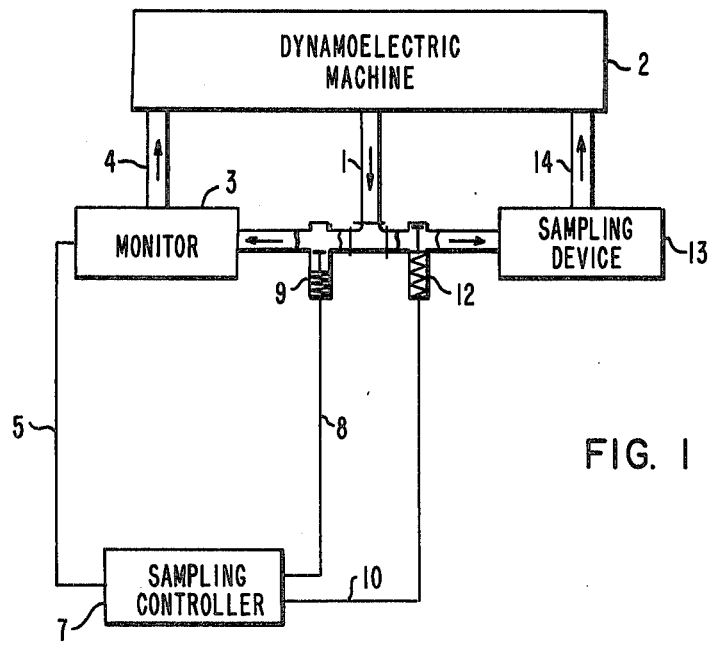
FIG. 1 is a diagram showing a gas-cooled dynamoelectric machine with a sampling system which has an improved sampling device in accordance with one embodiment of this invention.

In FIG. 1, conduit 1 carries gas from a gas stream of a dynamoelectric machine 2 to monitor 3 where it is monitored then returned to the dynamoelectric machine through conduit 4.

Monitor 3 checks the gas stream for any characteristics which indicate that thermal degradation of a material in the generator is occurring. (The thermal degradation may be due to primary failure of the material, or may be a secondary failure which indicates arcing or some other problem is occurring in the dynamoelectric machine.) Typically, the monitor checks the levels of particulates in the gas streams.

(The structure and operation of a principal form of gas stream monitor are more particularly described in U.S. Pat. No. 3,573,460 issued Apr. 6, 1971, and U.S. Pat. No. 3,427,880 issued Feb. 18, 1969.)

Particulates, which are small particles or condensed gases (i.e., liquids, aerosols) less than about 10 microns in size are formed when organic material thermally degrades. In fact, some of the materials in the machine may be coated with substances (sacrificial coatings) which produce large quantities of particulates at low temperatures to aid in the early detection of insulation failure. The monitor may also detect the failure of materials by checking the vapors in the gas streams.

Referring to FIG. 1 again, when the monitor detects failure of a material, it generates a first signal, typically an electric signal, which passes through line 5 to sampling controller 7.

Insulation occasionally falls off or is abraded off by friction and some of the dust can be made airborne by the moving parts of the generator. If these dust particles are present in sufficient quantities, they can cause monitor 3 to produce spurious signals for brief periods. These signals do not indicate a genuine material failure and may be ignored. Therefore, the sampling controller is not activated unless it receives a continuous signal for a predetermined length of time, typically on the order of fifteen seconds. It then produces a signal in line 8 which passes to solenoid valve means 9.

Since stopping a dynamoelectric machine and searching for insulation failure is a very expensive undertaking, monitor 3 must first be checked to determine that it is operating correctly. Depending on the type of monitor used, solenoid valve means 9 therefore terminates the flow of gas to the monitor, or more preferably diverts the gas through a filter (not shown) which filters out of the gas stream the particulates or gases that activated the monitor.

If the first signal from the monitor then terminates, sampling controller 7 generates a second signal which passes through line 10 to solenoid valve 12 which controls the flow of the gas stream to sampling device 13, then back to the dynamoelectric machine through conduit 14. Should the signal from the monitor not terminate shortly after solenoid valve means 9 is activated, then sampling controller 7 sends a signal which will indicate that there is a defective monitor.

Figure 2B:
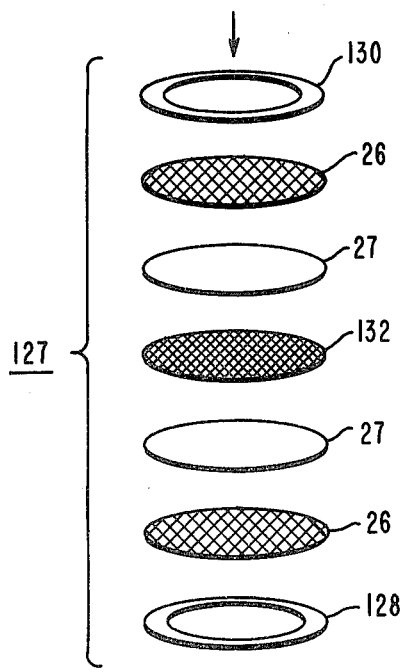
FIG. 2B is an expanded view of the principle elements of an improved trap in accordance with one embodiment of this invention.
Figure 2A:
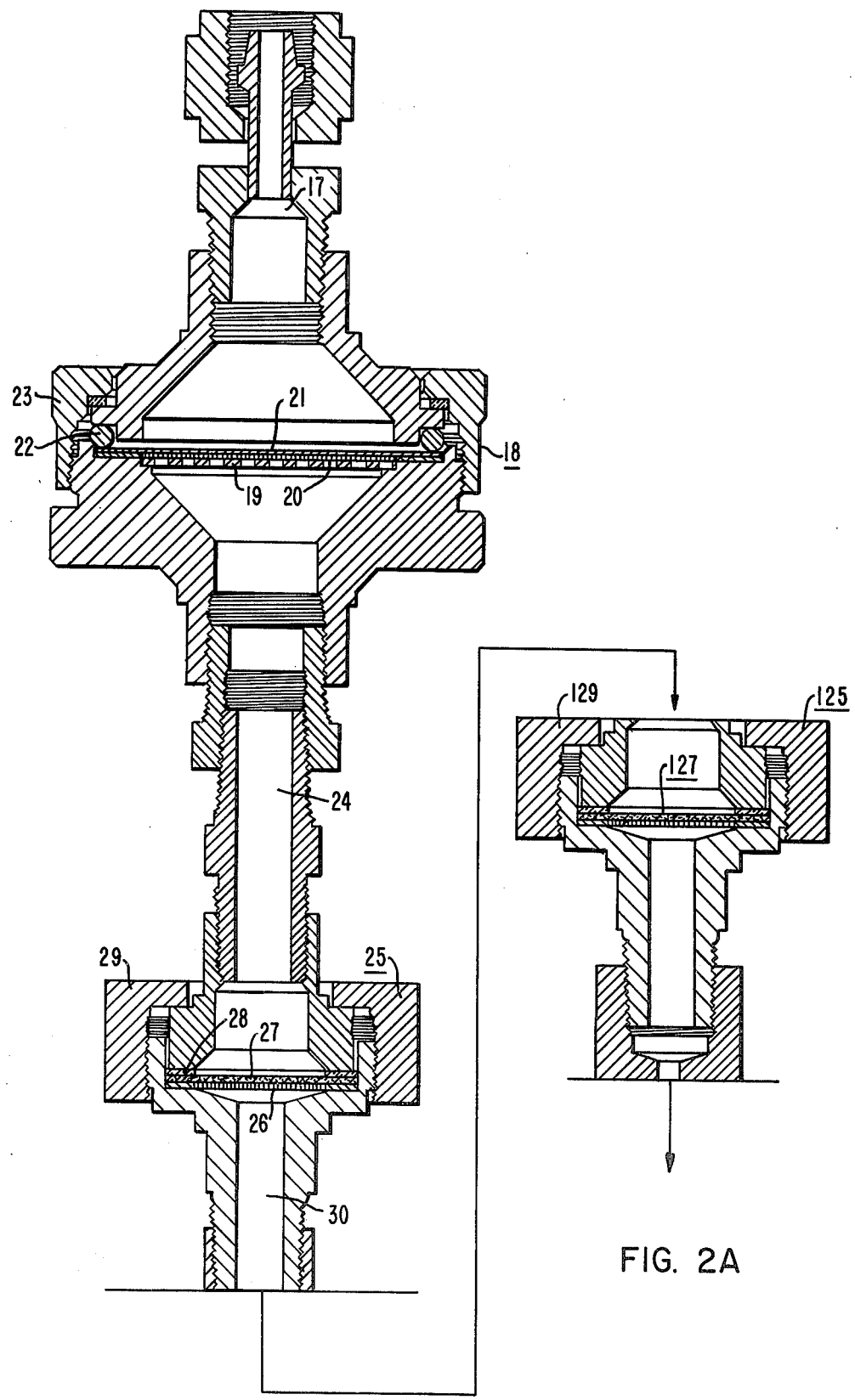
FIG. 2A is a side view in section of a sampling device according to one embodiment of this invention.

Particularly advantageous is the sampling device 13 shown in FIG. 2A because that device, like the prior art, separates the particulates from the large particles in the gas. It is the particulates which are most useful in analyzing which material was degraded.

In FIG. 2A the gas stream enters line 17 to particle filter chamber 18 where particles (i.e., greater than about 10 microns) are filtered out of the stream. The filter shown consists of grid 19 with support screen 20 which supports particle collector 21. The filter is held in place by gasket 22 and can be removed for analysis by unscrewing ring 23.

The gas stream then passes through line 24 to particulate filter chamber 25, where particulates (i.e., less than about 10 microns) are filtered out of the stream. The filter consists of screen 26, which supports particulate collector 27, a glass fiber disc of polypropylene, or other suitable materials. Collector 27 is held in place by gasket 28 and can be removed for analysis by unscrewing ring 29.

The gas stream then passes through line 30 to vapor trap 125. The vapor trap, as shown in FIG. 2B, contains a gasket 130, a screen 126, a glass fiber disc 27 adsorbing material 132, another glass fiber disc 27 and another screen 126 which prevents the material from being blown out by the gas pressure. The vapor trap 127 is held in place by gasket 128 and can be removed for analysis by unscrewing ring 129. The glass fiber discs prevent clogging of the screens by the adsorbing material. The adsorbing material 132 may be any material which adsorbs gas, such as activated carbon, silica gel, alumina, etc., but, as in the prior art, a modified ethylvinylbenzene-bivinylbenzene copolymer sold by Waters Company, under the trade name "POROPAK R" is preferred primarily because of its relatively insensitivity to water vapor normally present in a dynamoelectric machine atmosphere, which tends to mask the analysis of other trapped gases.

In the preferred embodiment, the particles are filtered out before the small particulates and the smaller particulates are filtered out before the gases.

The analysis of the collected material is made using mass spectrometry and/or other standard techniques, by comparing the results of the analysis to the results of analyzing the decomposition products of known dynamoelectric machine material. For example, each material used in the machine is slowly heated. When the monitor detects decomposition products, a sample is collected and analyzed, for example by a mass spectrometer. The mass spectrometer produces a chart of mass to charge ratios of each decomposition product produced by a particular material. The charts for the material used in the machines are compared to the charts of known samples and the unknown material is thereby identified. A "map" of the machine shows the location of each material used.

Figure 3A:
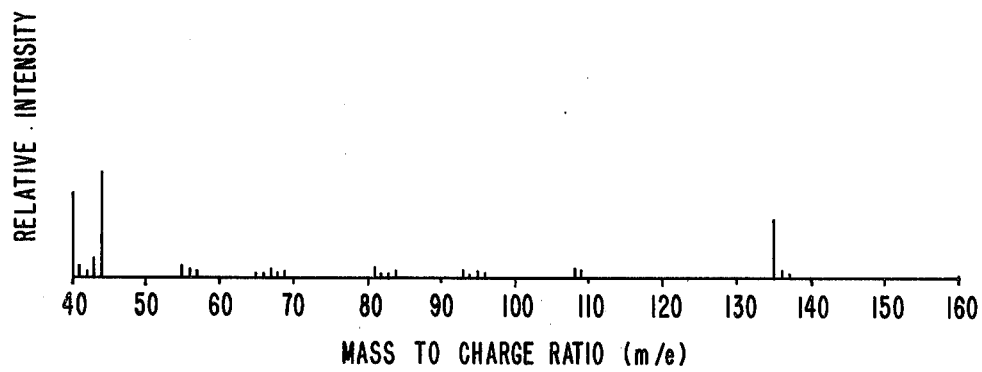
FIG. 3A is a mass spectrograph of particulates trapped using the prior art vapor trap.
Figure 3B:
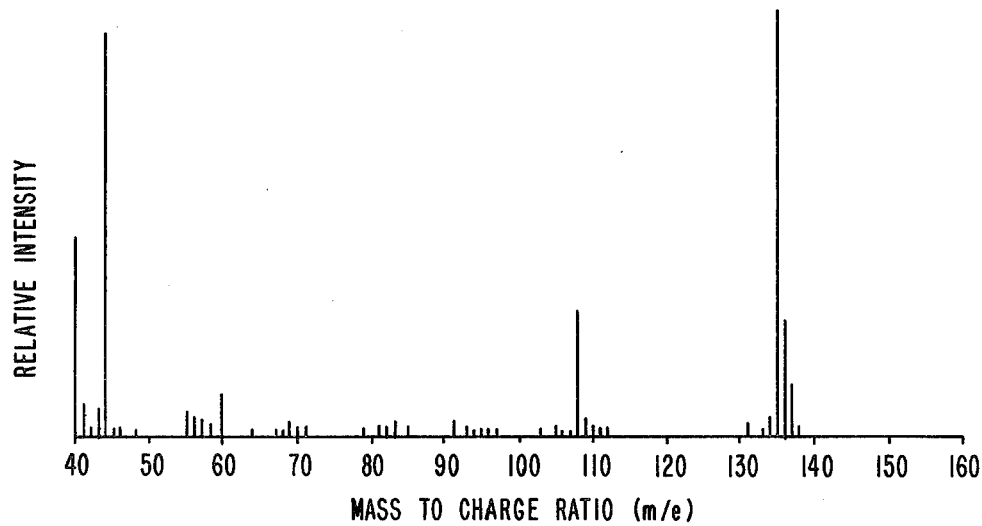
FIG. 3B is a mass spectrograph of the particulates trapped using the vapor trap of this invention.

The effectiveness of the invention as compared to the prior art is shown in FIGS. 3 and 4. FIG. 3A is the mass spectra of particulates collected in a particulate trap that was in a system that used the prior art style of vapor trap. FIG. 3B is a mass spectra of particulates collected on the prior art particulate trap that was followed by the vapor trap of this invention. (FIG. 3A involved the thermal particulation of 120 milligrams of insulation material in the laboratory. Because of limited available samples, FIG. 3B involved the particulation of only 67 milligrams of the same material.) By comparing the spectrograms of FIG. 3A to 3B, the results show a substantial improvement on sensitivity in FIG. 3B over FIG. 3A. This is attributed to the fact that the disclosed vapor trap offers very low resistance to the gas stream flow which facilitates a better sample of the particulates being collected.

Figure 4A:
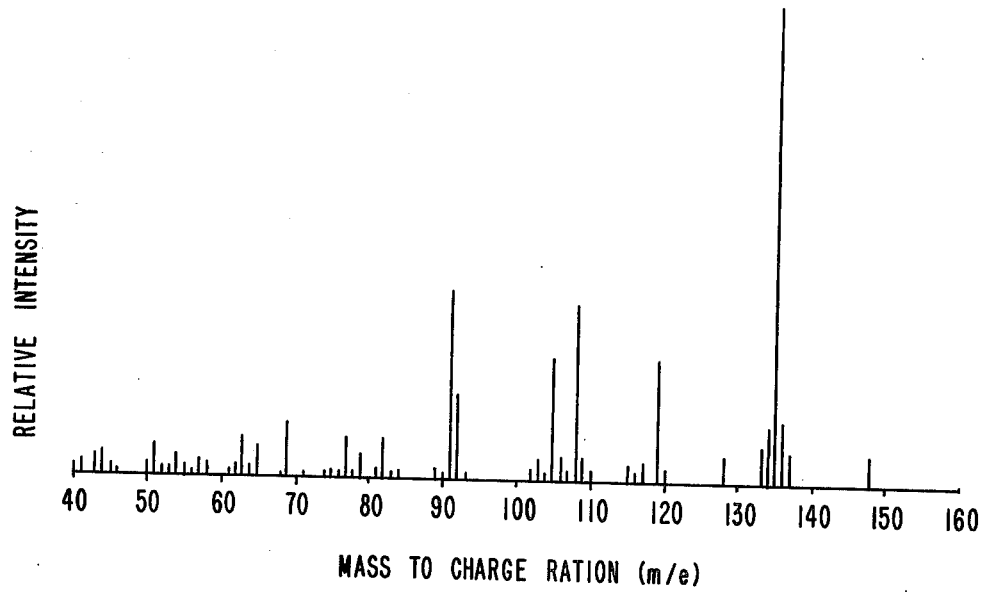
FIG. 4A is a mass spectrograph of vapors collected by the prior art vapor trap.
Figure 4B:
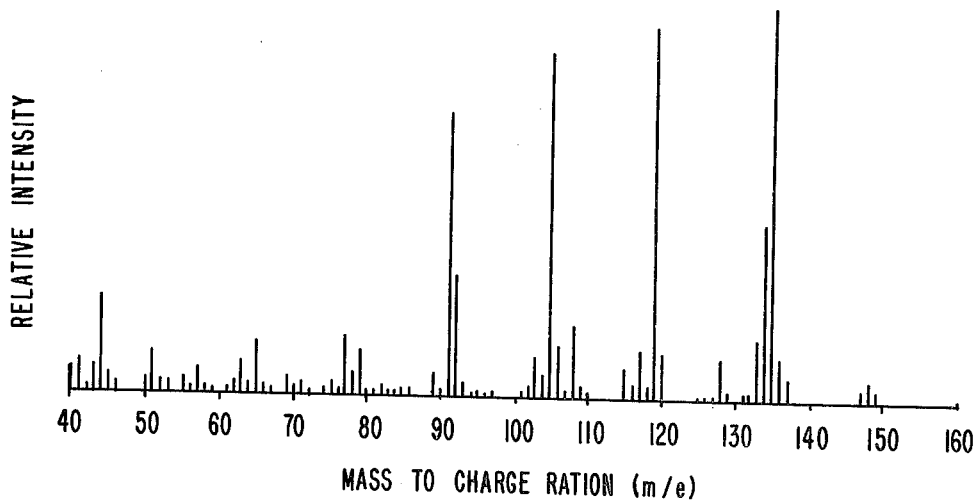
FIG. 4B is a mass spectrograph of vapors collected by the vapor trap of this invention.

FIGS. 4A and 4B show the mass spectra of vapor effluents collected concurrently with the particulate effluents of FIGS. 3A and 3B, respectively. It shows the device of this invention continues to effectively trap organic vapors. A comparison of FIGS. 3B, 4A and 4B also shows that the particulate matter causing monitor alarm can pass through the present particulate collector in the vapor state. FIG. 4A is rich in signals at mass to energy ratio 108 and 135; relative to its mass to energy ratios at 91, 92, 105, 119, 134. Also, it shows that the same peaks were depleted in the mass spectra of FIG. 4B.

We claim:

1. In a multi-part sampler for use in a gas stream monitoring system of a gas-cooled dynamoelectric machine, the sampler comprising: a first part including a filter means for trapping particles of greater than about 10 microns across, a second part including a particulate collector means for trapping particulates of less than about 10 microns across, and a third part for trapping vapor, said third part comprising a vapor-adsorbing material in a thin layer having a thickness that is a small fraction of its surface layer diameter that is transverse the direction of the gas stream such that the gas flow resistance of the third part is essentially zero.

2. The multi-part sampler as defined by claim 1 wherein: said vapor adsorbing layer comprises a modified ethylvinylbenzene-divinylbenzene copolymer.

3. The multi-part sampler as defined in claim 2 wherein:
said third part of the sampler comprises, in sequential arrangement, a first annular sealing gasket, a first disc-shaped screen, a first glass fiber disc, said thin layer of vapor-adsorbing material, a second glass fiber disc, a second disc-shaped screen, and a second annular sealing gasket.